(12) United States Patent
Fujii

(10) Patent No.: US 7,595,298 B2
(45) Date of Patent: *Sep. 29, 2009

(54) POLYPEPTIDES HAVING ANTI-HIV ACTIVITY AND COMPOSITIONS COMPRISING SAME

(75) Inventor: Nobutaka Fujii, Ohtsu (JP)

(73) Assignee: Biokine Therapeutics Ltd., Rehovot (IL)

( * ) Notice: Subject to any disclaimer, the term of this patent is extended or adjusted under 35 U.S.C. 154(b) by 128 days.

This patent is subject to a terminal disclaimer.

(21) Appl. No.: 11/497,225

(22) Filed: Aug. 1, 2006

(65) Prior Publication Data

US 2006/0264605 A1    Nov. 23, 2006

Related U.S. Application Data

(62) Division of application No. 10/363,209, filed as application No. PCT/JP01/07668 on Sep. 5, 2001, now Pat. No. 7,138,488.

(30) Foreign Application Priority Data

Sep. 5, 2000 (JP) .............................. 2000-269296
Mar. 28, 2001 (JP) .............................. 2001-092306

(51) Int. Cl.
*A61K 38/00* (2006.01)
*C07K 2/00* (2006.01)
*C07K 4/00* (2006.01)
*C07K 5/00* (2006.01)
*C07K 14/00* (2006.01)
*C07K 16/00* (2006.01)
*C07K 17/00* (2006.01)
*A61K 39/12* (2006.01)
*A61K 39/21* (2006.01)

(52) U.S. Cl. ..................... 514/14; 530/300; 424/204.1; 424/208.1

(58) Field of Classification Search ................ None
See application file for complete search history.

(56) References Cited

U.S. PATENT DOCUMENTS

2006/0264378 A1    11/2006 Fujii et al. ..................... 514/14

FOREIGN PATENT DOCUMENTS

WO    WO 95/10534    4/1995
WO    WO 99/47158    9/1999
WO    WO 01/64716    9/2001

OTHER PUBLICATIONS

2000 Development of Specific CXCR4 Inhibitors Based on an Anti-HIV Peptide, T140, and Their Structure-Activity Relationships Study Akane Omagari et al. Peptide Science vol. 2000, No. 37th 129-132.
Sep. 14, 2000 Pharmacophore Identification of a Specific CXCR4 Inhibitor, T140, Leads to Development of Effective Anti-HIV Agents with Very High Selectivity Indexes Hirokazu Tamamura et al. Bioorganic & Medical Chemistry Letters vol. 10, No. 23 2633-2637.
Mar. 2001 Increase of R5 HIV-1 Infection and CCR5 Expression in T Cells Treated With High Concentration of CXCR4 Antagonists and SDF-1 Kazuko Gotoh et al. Journal of Infection and Chemotherapy vol. 7, No. 1 28-36.
1998 HIV-cell Fusion Inhibitors Targeted to the HIV Second Receptor: T22 and Its Downsized Analogs with High Activity Hirokazu Tamamura et al. Peptide Science vol. 1998, No. 35 49-52.
Dec. 30, 1998 A Low-Molecular-Weight Inhibitor against the Chemokine Receptor CXCR4: A Strong Anti-HIV Peptide T140 Hirokazu Tamamura et al. Biochemical and Biophysical Research Communications vol. 253, No. 3 877-882.
Oct. 16, 1997 Effective Lowly Cytotoxic Analogs of an HIV-cell Fusion Inhibitor, T22([Tyr5,12, Lys7]-polyphemusin II) Hirokazu Tamamura et al. Bioorganic & Medical Chemistry vol. 6, No. 2 231-238.
Feb. 1, 1999 "T134, a Small Molecule CXCR4 Inhibitor, Has No Cross-Drug Resistance with AMD3100, a CXCR4 Antagonist with a Different Structure" Rieko Arakaki et al. Journal of Virology vol. 73, No. 2 pp. 1719-1723.
Nakashima H. et al., "Anti-human immunodeficiency virus activity of a novel synthetic peptide, T22 ([Tyr-5,12, Lys-7]polyphemusin II): a possible inhibitor of virus-cell fusion". Antimicrob Agents Chemother. Jun. 1992;36(6):1249-55.
Tamamura et al., "Downsizing of an HIV-cell fusion inhibitor, T22 ([Tyr5,12, Lys7]-polyphemusin II), with the maintenance of anti-HIV activity and solution structure". B ioorg Med Chem. Apr. 1998;6(4):473-9.

*Primary Examiner*—Anish Gupta
*Assistant Examiner*—Marcela M Cordero Garcia
(74) *Attorney, Agent, or Firm*—Jordan and Hamburg LLP

(57) ABSTRACT

The present invention relates to a polypeptide represented by the formula:

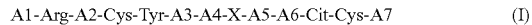

A1-Arg-A2-Cys-Tyr-A3-A4-X-A5-A6-Cit-Cys-A7    (I)

(wherein A1 represents a hydrogen atom or an arginine, lysine, ornithine, citrulline, alanine residue, etc.; A2 represents an aromatic amino acid residue; A3, A4 and A6 represent an arginine, lysine, ornithine, citrulline or alanine residue, A5 represents a tyrosine, phenylalanine, alanine, naphthylalanine or citrulline residue; A7 represents a lysine or arginine residue in which a carboxyl group may be amidated; X represents a D-ornithyl-proline, prolyl-D-ornithine, D-lysyl-proline residue, etc.; provided that either of A1, A3, A4, A5, A6 and A7 is an alanine residue, etc., or X is citrulline, etc.) or a salt thereof.

18 Claims, 2 Drawing Sheets

POLYPEPTIDES HAVING ANTI-HIV ACTIVITY AND COMPOSITIONS COMPRISING SAME

TECHNICAL FIELD

The present invention relates to a novel polypeptide and a medicine containing said polypeptide as an effective ingredient such as an anti-HIV virus agent, etc.

Since antiviral activity of an endotoxin-affinity polypeptide separated from horseshoe crab (*Tachypleus* genus, *Limulus* genus and *Carcinoscopius* genus) has been found out (Japanese Provisional Patent Publication No. 2-167230 and Japanese PCT Provisional Patent Publication No. 2-500194), many attempts to synthesize novel antiviral polypeptides have been carried out by chemical modification thereof, reducing a molecular weight thereof and modifying a part of the structure of the above-mentioned polypeptide (WO92/04374, Japanese Provisional Patent Publication No. 5-163298 and Japanese PCT Provisional Patent Publication No. 8-504837). In recent years, it has been found out that novel low molecular weight antiviral polypeptides T134 and T140 are polypeptides having low cytotoxicity and having excellent anti-HIV virus activity (H. Tamamura et. al.; Biochemical and Biophysical Research Commun., 253, 877-882 (1998)). However, these T134 and T140 were not practical for a medical use.

Accordingly, an object of the present invention is to provide a polypeptide having excellent anti-HIV virus activity and low cytotoxicity.

The present inventor has earnestly carried out studies to solve the above-mentioned problems. As a result, he has found out that a novel polypeptide shows an excellent anti-HIV virus activity and has low cytotoxicity, in which a part of amino acids of T140, which has conventionally been known to inhibit infection of HIV by specifically binding to a CXCR4 ligand, is substituted with other amino acids, whereby he has accomplished the present invention.

DISCLOSURE OF THE INVENTION

That is, the present invention relates to a novel polypeptide represented by the following formula (I):

```
                                        (SEQ ID NO: 18)
1   2    3   4    5    6    7  8 9  10 11  12   13
A1-Arg-A2-Cys-Tyr-A3-A4-X-A5-A6-Cit-Cys-A7  (I)
```

(wherein

A1 represents a hydrogen atom, or an arginine, lysine, ornithine, citrulline or alanine residue or a residue of N-α-substituted derivative of these amino acids;

A2 represents an aromatic amino acid residue;

A3, A4 and A6 each independently represent an arginine, lysine, ornithine, citrulline or alanine residue;

A5 represents a tyrosine, phenylalanine, alanine, naphthylalanine or citrulline residue;

A7 represents a lysine or arginine residue in which a carboxyl group may be amidated;

X represents a peptide residue represented by the following formula (a):

```
 1'  2'  3'   4'   5'   6'
-A8-A9-A10-Gly-A11-A12-         (a)
```

(wherein

A8 and A12 each independently represent an alanine, valine, leucine, isoleucine, serine, cysteine or methionine residue;

A9 represents an aromatic amino acid residue, A10 is selected from the same amino acid residues as in A3, A11 represents a tyrosine, phenylalanine, tryptophane, alanine, valine, leucine, isoleucine, serine, cysteine or methionine residue, provided that when both of the 1'-position and the 6'-position are cysteine residues, they may be bonded by a disulfide bond), or a peptide residue selected from the group consisting of a D-ornithyl-proline, prolyl-D-ornithine, D-lysyl-proline, prolyl-D-lysine, D-arginyl-proline, prolyl-D-arginine, D-citrullyl-proline, D-citrullyl-alanine, D-alanyl-citrulline, prolyl-D-citrulline, glycyl-ornithine, ornithyl-glycine, glycyl-lysine, lysyl-glycine, glycyl-arginine, arginyl-glycine, glycyl-citrulline, citrullyl-glycine, D-alanyl-proline, and D-lysyl-alanine, and a hydrogen atom of a side chain ω-amino group of D-arginine, L-arginine, D-lysine, L-lysine, D-ornithine or L-ornithine which are constitutional amino acids of said peptide residues may be substituted by a ω-aminoacyl group, and these peptide residues represent a peptide residue which binds amino acid residues at the 7-position and the 9-position through a peptide bond;

wherein Arg represents an arginine residue, Cys represents a cysteine residue, Tyr represents a tyrosine residue, Cit represents a citrulline residue, Gly represents a glycine residue, and the cysteine residues at the 4-position and the 12-position may be bonded by a disulfide bond;

provided that, in the above polypeptide or a salt thereof,
either of the amino acid residues of A1, A3, A4, A5 and A6 is an alanine or citrulline residue; or
X represents a peptide residue containing a D-citrulline, D-alanine, citrulline or alanine residue) or a salt thereof.

In the polypeptides of the formula (I) of the present invention, A1 is preferably an arginine, alanine or citrulline residue; A2 is preferably a tryptophane or naphthyl-alanine residue; A3 is preferably arginine, alanine or citrulline residue; A4 is preferably a lysine, alanine or citrulline residue; X is preferably a D-lysyl-proline, D-alanyl-proline, D-lysyl-alanine or D-citrullyl-proline residue; A5 is preferably a tyrosine or alanine residue; A6 is preferably an arginine, alanine or citrulline residue; A7 is preferably an arginine residue.

Specific examples of the most preferred polypeptide of the present invention is a polypeptide of the formula (I) wherein A1, A6 and A7 are arginine residues, A2 is a naphthylalanine residue, A3 is a citrulline residue, A4 is a lysine residue, X is a D-lysyl-proline residue, and A5 is a tyrosine residue (SEQ ID NO: 20), a polypeptide of the formula (I) wherein A1, A3, A6 and A7 are arginine residues, A2 is a naphthylalanine residue, A4 is a lysine residue, X is a D-citrullyl-proline residue, and A5 is a tyrosine residue (SEQ ID NO: 21), a polypeptide of the formula (I) wherein A1, A6 and A7 are arginine residues, A2 is a naphthylalanine residue, A3 is a citrulline residue, A4 is a lysine residue, X is a D-citrullyl-proline residue, and A5 is a tyrosine residue (SEQ ID NO: 22), and a polypeptide of the formula (I) wherein A1 is a citrulline residue, A2 is a naphthylalanine residue, A3, A6 and A7 are arginine residues, A7 having a carboxyl group amidated, A4 is a lysine residue, X is a D-citrullyl-proline residue, and A5 is a tyrosine residue (SEQ ID NO: 16).

As another embodiment of the preferred polypeptide according to the present invention, there may be exemplified by a polypeptide of the formula (I) wherein A1, A6 and A7 are arginine residues, A2 is a naphthylalanine residue, A3 is a alanine residue, A4 is a lysine residue, X is a D-lysyl-proline residue, and A5 is a tyrosine residue (SEQ ID NO: 4), a polypeptide of the formula (I) wherein A1 is a citrulline residue, A2 is a naphthylalanine residue, A3, A6 and A7 are arginine residues, A4 is a lysine residue, X is a D-lysyl-proline residue, and A5 is a tyrosine residue (SEQ ID NO: 10), a polypeptide of the formula (I) wherein A1, A3 and A7 are arginine residues, A2 is a naphthylalanine residue, A4 is a lysine residue, X is a D-lysyl-proline residue, A5 is a tyrosine residue, and A6 is a citrulline residue (SEQ ID NO: 14), a polypeptide of the formula (I) wherein A1 and A3 are citrulline residues, A2 is a naphthylalanine residue, A4 is a lysine residue, X is a D-lysyl-proline residue, A5 is a tyrosine residue, A6 and A7 are arginine residues (SEQ ID NO: 19), and a polypeptide of the formula (I) wherein A1, A3 and A7 are arginine residues, A2 is a naphthylalanine residue, A4 is a lysine residue, X is a D-citrullyl-proline residue, A5 is a tyrosine residue, and A6 is a citrulline residue (SEQ ID NO: 17).

Incidentally, in the polypeptide of the present invention, the amino acid of A7 is preferably one in which the carboxyl group is amidated in view of improving stability of the polypeptide in vivo such as in serum, etc.

Specific examples of the polypeptides of the present invention are shown in the following Table 1 together with the conventionally known polypeptides T134 and T140.

In the polypeptide of the above-mentioned formula, respective symbols mean amino acid residues shown by three-letter code internationally admitted, and all amino acids mean L-amino acids otherwise it is shown as D-amino acid in which the character "D" is put in front of said three-letter code, Nal represents L-3-(2-naphthyl)alanine, and Cit represents L-citrulline [=2-amino-5-ureidovalerianic acid].

BEST MODE FOR CARRYING OUT THE INVENTION

Figure 1:
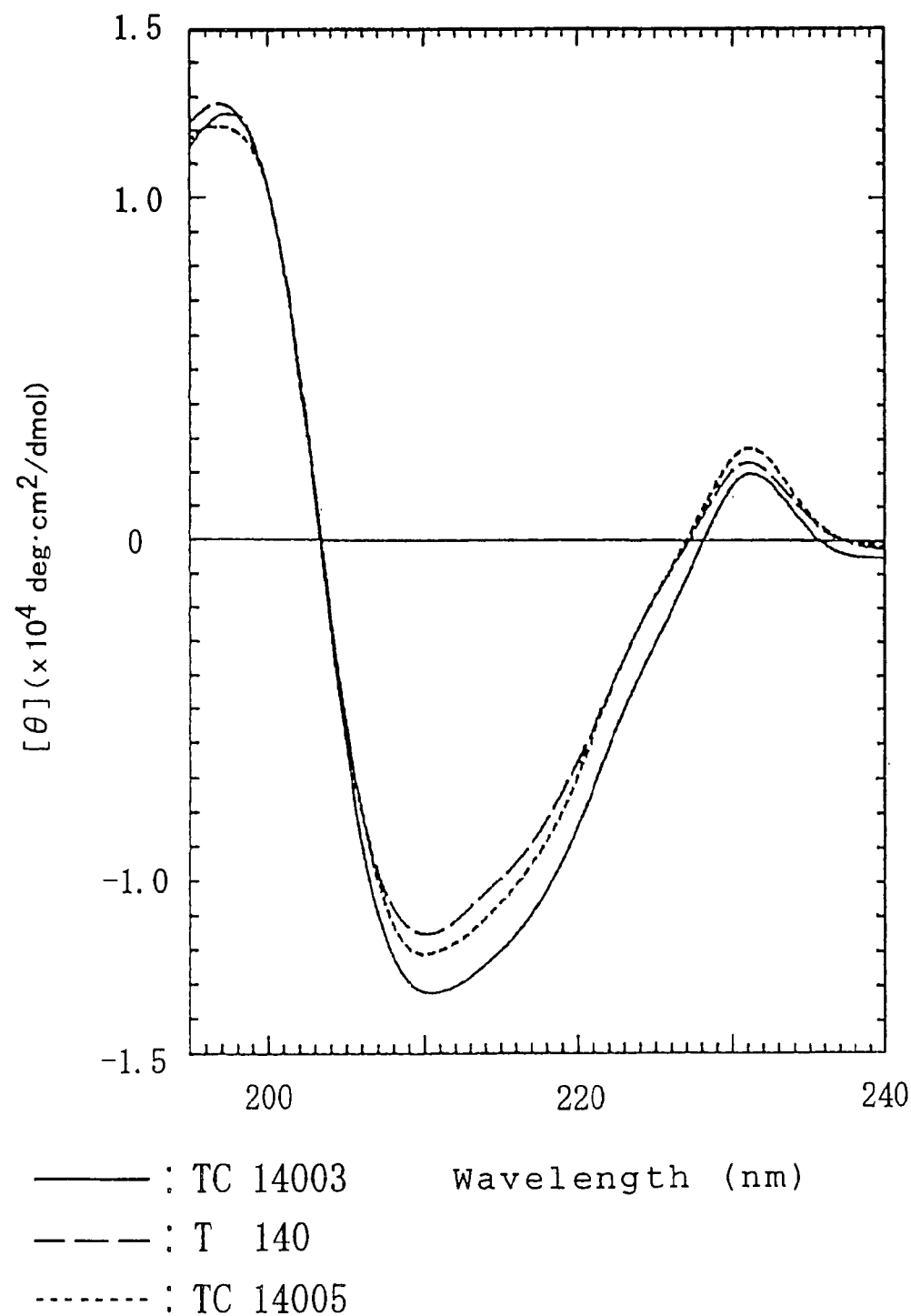
FIG. 1 is CD spectra of polypeptides TC14003 and TC14005 of the present invention, and T140.

The polypeptide of the formula (I) according to the present invention can be produced by a polypeptide synthetic method, for example, a solid phase peptide synthesis, a liquid phase peptide synthesis and the like. In the solid phase synthesis, the peptide can be produced by, for example, bonding a carboxyl group of a N-protected arginine (or lysine) in which an α-amino group of an amino acid corresponding to A7 is protected by an urethane type protecting group such as 9-fluorenylmethyloxycarbonyl (Fmoc) group, etc., to an

TABLE 1

| SEQ ID NO. | | 1 (A1) ① | 2 (A2) ② | 3 ③ | 4 ④ | 5 ⑤ | 6 (A3) ⑥ | 7 (A4) ⑦ | 8 X ⑧ | 9 (A5) ⑨ | 10 (A6) ⑩ | 11 ⑪ | 12 ⑫ | 13 (A7) ⑬ ⑭ |
|---|---|---|---|---|---|---|---|---|---|---|---|---|---|---|
| 1 | T134* | H-Arg-Arg-Trp-Cys-Tyr-Arg-Lys-DLys-Pro-Tyr-Arg-Cit-Cys-Arg-OH |
| 2 | T140* | H-Arg-Arg-Nal-Cys-Tyr-Arg-Lys-DLys-Pro-Tyr-Arg-Cit-Cys-Arg-OH |
| 3 | TA14001 | H-Ala-Arg-Nal-Cys-Tyr-Arg-Lys-DLys-Pro-Tyr-Arg-Cit-Cys-Arg-OH |
| 4 | TA14005 | H-Arg-Arg-Nal-Cys-Tyr-Ala-Lys-DLys-Pro-Tyr-Arg-Cit-Cys-Arg-OH |
| 5 | TA14006 | H-Arg-Arg-Nal-Cys-Tyr-Arg-Ala-DLys-Pro-Tyr-Arg-Cit-Cys-Arg-OH |
| 6 | TA14007 | H-Arg-Arg-Nal-Cys-Tyr-Arg-Lys-DLys-Pro-Tyr-Arg-Cit-Cys-Arg-OH |
| 7 | TA14008 | H-Arg-Arg-Nal-Cys-Tyr-Arg-Lys-DLys-Ala-Tyr-Arg-Cit-Cys-Arg-OH |
| 8 | TA14009 | H-Arg-Arg-Nal-Cys-Tyr-Arg-Lys-DLys-Pro-Ala-Arg-Cit-Cys-Arg-OH |
| 9 | TA14010 | H-Arg-Arg-Nal-Cys-Tyr-Arg-Lys-DLys-Pro-Tyr-Ala-Cit-Cys-Arg-OH |
| 10 | TC14001 | H-Cit-Arg-Nal-Cys-Tyr-Arg-Lys-DLys-Pro-Tyr-Arg-Cit-Cys-Arg-OH |
| 20 | TC14003 | H-Arg-Arg-Nal-Cys-Tyr-Cit-Lys-DLys-Pro-Tyr-Arg-Cit-Cys-Arg-OH |
| 11 | TN14003 | H-Arg-Arg-Nal-Cys-Tyr-Cit-Lys-DLys-Pro-Tyr-Arg-Cit-Cys-Arg-NH$_2$ |
| 12 | TC14004 | H-Arg-Arg-Nal-Cys-Tyr-Arg-Cit-DLys-Pro-Tyr-Arg-Cit-Cys-Arg-OH |
| 21 | TC14005 | H-Arg-Arg-Nal-Cys-Tyr-Arg-Lys-DCit-Pro-Tyr-Arg-Cit-Cys-Arg-OH |
| 13 | TN14005 | H-Arg-Arg-Nal-Cys-Tyr-Arg-Lys-DCit-Pro-Tyr-Arg-Cit-Cys-Arg-NH$_2$ |
| 14 | TC14006 | H-Arg-Arg-Nal-Cys-Tyr-Arg-Lys-DLys-Pro-Tyr-Cit-Cit-Cys-Arg-OH |
| 22 | TC14011 | H-Arg-Arg-Nal-Cys-Tyr-Cit-Lys-DCit-Pro-Tyr-Arg-Cit-Cys-Arg-OH |
| 15 | TC14012 | H-Arg-Arg-Nal-Cys-Tyr-Cit-Lys-DCit-Pro-Tyr-Arg-Cit-Cys-Arg-NH$_2$ |
| 16 | TC14018 | H-Cit-Arg-Nal-Cys-Tyr-Arg-Lys-DCit-Pro-Tyr-Arg-Cit-Cys-Arg-NH$_2$ | insoluble resin through a spacer which is optionally capable of bonding to the carboxyl group (that is, the carboxyl group of arginine (or lysine) is converted into p-carboxymethylbenzyl ester), then, removing the protecting group for the α-amino group, linking N-protected cysteine thereto, and carrying out condensation of amino groups successively to an amino terminus direction in the same manner as mentioned above. In other words, the protected amino acids corresponding to the 12-position to the 1-position of the amino acid sequence shown by the following formula (I) are successively linked according to the solid phase synthesis, then, the protecting groups bound to the insoluble resin and respective amino acids are eliminated to obtain the straight chain polypeptide of the present invention represented by the above-mentioned formula (I). Moreover, in the obtained polypeptide, two cysteines at the 4-position and the 12-position can form a disulfide bond (—S—S—) through a mercapto group.

```
                                                  (SEQ ID NO: 18)
1  2    3   4   5  6  7 8  9  10 11  12  13
A1-Arg-A2-Cys-Tyr-A3-A4-X-A5-A6-Cit-Cys-A7  (I)
```

(wherein

A1 represents a hydrogen atom or an arginine, lysine, ornithine, citrulline or alanine residue, or a residue of N-α-substituted derivative of these amino acids;

A2 represents an aromatic amino acid residue, preferably a tyrosine, phenylalanine, tryptophane or naphthyl-alanine residue;

A3, A4 and A6 each independently represent an arginine, lysine, ornithine, citrulline or alanine residue;

A5 represents a tyrosine, phenylalanine, alanine, naphthylalanine or citrulline residue;

A7 represents a lysine or arginine residue in which the carboxyl group may be amidated;

X represents a peptide residue represented by the following formula (a):

```
      1' 2'  3'   4'  5'  6'
     -A8-A9-A10-Gly-A11-A12-            (a)
```

(wherein

A8 or A12 represents an alanine, valine, leucine, isoleucine, serine, cysteine or methionine residue;

A9 represents an aromatic amino acid residue, A10 is selected from the same amino acid residues as in A3, A11 represents a tyrosine, phenylalanine, tryptophane, alanine, valine, leucine, isoleucine, serine, cysteine or methionine residue, provided that when both of the 1'-position and the 6'-position are cysteine residues, these may be bonded by a disulfide bond), or a peptide residue selected from the group consisting of D-ornithyl-proline, prolyl-D-ornithine, D-lysyl-proline, prolyl-D-lysine, D-arginyl-proline, prolyl-D-arginine, D-citrullyl-proline, prolyl-D-citrulline, D-citrullyl-alanine, D-alanyl-citrulline, glycyl-ornithine, ornithyl-glycine, glycyl-lysine, lysyl-glycine, glycyl-arginine, arginyl-glycine, glycyl-citrulline, citrullyl-glycine, D-alanyl-proline, and D-lysyl-alanine, and a hydrogen atom of a side chain ω-amino group of D-arginine, L-arginine, D-lysine, L-lysine, D-ornithine or L-ornithine which are constitutional amino acids of said peptide residues may be substituted by a ω-acylamino group, and these peptide residues represent a peptide residue which binds amino acid residues at the 7-position and the 9-position through a peptide bond;

wherein, Arg represents an arginine residue, Cys represents a cysteine residue, Tyr represents a tyrosine residue, Cit represents a citrulline residue, Gly represents a glycine residue;

in the above-mentioned polypeptide or a salt thereof, either of the amino acid residues of A1, A3, A4, A5 and A6 is an alanine or citrulline residue, or;

X is a peptide residue containing a D-citrulline, D-alanine, citrulline or alanine residue).

As the above-mentioned insoluble resin having an amino group, any material may be used so long as it is capable of binding to a carboxyl group of an N-protected arginine (or lysine) at the C-terminus or a spacer (a cross-linking group) optionally bonding thereto, and capable of being eleminated after synthesis of a polypeptide.

As such an insoluble resin, there may be mentioned, for example, Alko resin (p-benzyloxyalcohol resin), a benzhydrylamine resin, a methylbenzhydrylamine resin, an aminomethylphenoxymethyl resin, a Fmoc-NH-SAL resin [(4-(2',4'-dimethoxyphenyl-Fmoc-aminoethyl)phenoxy linker resin), H. Rink, Tetrahedron Lett., 28: 3787(1987), 0.68 mmole/g] and derivatives of these materials, etc. When these resins are used, an objective material can be directly obtained therefrom by cleavage in either of the cases, and in view of a yield, Alko resin or a Fmoc-NH-SAL resin is preferred.

As the above-mentioned spacer optionally bonding to the carboxyl group of the amino acid at the C-terminus, there may be mentioned a spacer having a functional group capable of bonding to the carboxyl group and a carboxyl group, and there may be mentioned, for example, that which can convert the carboxyl group of arginine (or lysine) to a p-carboxymethylbenzyl ester, but it is not specifically limited.

The protected amino acid to be used for synthesis of the polypeptide of the present invention means an amino acid whose functional group is protected by a protecting group according to the conventionally known method, and various kinds of protected amino acid are commercially available. When the polypeptide of the present invention is to be synthesized, either of the protecting groups shown below is preferably selected. First, as the protecting group for an α-amino group of an amino acid, Boc (t-butyl-oxycarbonyl) or Fmoc (9-fluorenylmethyloxycarbonyl) is preferred. As the protecting group for a guanidino group of arginine (Arg), Tos (tosyl), $NO_2$ (nitro), Mtr (4-methoxy-2,3,6-trimethylbenzenesulfonyl), Pmc (2,2,5,7,8-pentamethylchroman-6-sulfonyl) or Pbf (2,2,4,6,7-penta-hydroxydihydrobenzofuran-6-sulfonyl) is preferred. As the protecting group for a mercapto group of cysteine, there may be mentioned Bzl (benzyl), 4-MeOBzl (4-methoxybenzyl), 4-MeBzl (4-methylbenzyl), Acm (acetamidomethyl), Trt (tri-tyl), Npys (3-nitro-2-pyridinesulfenyl), t-Bu (t-butyl) and t-Bus (t-butylthio), and 4-MeBzl, Acm, or Npys is preferred. As the protecting group for a hydroxyl group of tyrosine (Tyr), Bzl, $Cl_2Bzl$ (2,6-dichlorobenzyl) or t-Bu may be mentioned, or it may not be protected. As the protecting group for an ε-amino group of lysine (Lys), there may be mentioned Z (benzyloxycarbonyl), 2-ClZ (2-chlorobenzyloxycarbonyl), Boc or Npys. It is preferred that the respective protecting groups are selected from the already known protecting groups, depending on the synthetic conditions of a peptide.

In synthesis of a peptide, linking of a protected amino acid can be carried out according to an ordinary condensation method such as DCC (dicyclohexylcarbodiimide) method, DIPCDI (diisopropylcarbodiimide) method [Tartar, A. et. al.:

J. Org. Chem. 44, 5000 (1979)], active ester method, mixed or symmetric acid anhydride method, carbonyl-diimidazole method, DCC-HOBt (1-hydroxybenzotriazole) method [Keonig, W. et. al.: Chem. Ber., 103, 788, 2024, 2034 (1970)], diphenylphosphorylazide method and the like, and the DCC method, DCC-HOBt method, DIPCDI-HOBt method or symmetric acid anhydride method is preferred. These condensation reactions are generally carried out in an organic solvent such as dichloromethane, dimethylformamide, etc., or in a mixed solvent of the above-mentioned solvents. As the eliminating reagent of the protecting group for an α-amino group, there may be used trifluoroacetic acid/dichloromethane, HCl/dioxane, piperidine/dimethylformamide, etc., and they are suitably selected depending on the kind of said protecting group. Also, a degree of the progress of the condensation reaction at respective stages of synthesis can be examined by a method of E. Kaiser, et. al. [Anal, Biochem., 34, 595 (1970)] (ninhydrin reaction method).

As described above, a protected polypeptide having a desired amino acid sequence can be obtained.

When an aminomethyl resin derivative is used as the insoluble resin, the protected polypeptide can be eliminated from said resin by, for example, treating with ammonia in a suitable solvent. Subsequently, by treating the resulting material by hydrogen fluoride, polypeptide amide in which all the protecting groups are eliminated shown by the above formula can be obtained. When a benzhydrylamine resin, methylbenzhydrylamine resin, aminomethylphenoxymethyl resin or DMBHA resin [Funakoshi. S. et. al.; J. Chem. Soc., Chem. Commun., 1988, 382] is used as the insoluble resin, said resin and the protecting groups are simultaneously eliminated by treating it with hydrogen fluoride, TFMSA (trifluoromethane sulfonic acid) [published by Academic Press, edited by E. Gross, Yajima, H.; "The Peptides" vol 5, P65 (1983)], TMSOTf (trimethylsilyltrifurate) [Fujii, N. et. al.; J. Chem. Soc., Che. Commun., 1987, 274] or TMSBr (trimethylsilyl bromide) [Fujii, N. et. al.; Chem. Pharm. Bull., 35, 3880 (1987)] and the like.

Further, a cyclic polypeptide can be obtained by reducing with 2-mercaptoethanol, DTT (dithiothreitol), etc. to make a mercapto group of cysteine a reduced type, if desired, and then, subjecting to oxidation treatment to form a disulfide bond.

For the oxidation treatment, a method already known in the art can be used, and oxygen in air or an oxidizing agent such as ferricyanate (for example, potassium ferricyanide) is usually employed.

Incidentally, an anti-HIV substance is bonded to the above-mentioned polypeptide which is in a state of bonding to a resin, to form a complex of the polypeptide according to the present invention and the anti-HIV substance. As the above-mentioned anti-HIV substance, there may be mentioned, for example, a reverse transcriptase inhibitor, a HIV protease inhibitor and the like.

As the above-mentioned reverse transcriptase inhibitor, there may be mentioned a substance which inhibits activity of reverse transcriptase of HIV, and nucleoside type and non-nucleoside type substances may be mentioned. As the nucleoside type inhibitor, a nucleoside or an analogue thereof constituted by either of a base selected from a pyrimidine base, a purine base, an imidazole base and a triazole base, and a furanose having at least one hydroxyl group or its acyclo derivative is preferred, and there may be mentioned, for example, AZT (CAS REGISTRY NUMBERS: 30516-87-1: zidovudine), ddI (CAS REGISTRY NUMBERS: 69655-05-6: didanosine), ddC (CAS REGISTRY NUMBERS: 7481-89-2: zalcitabine), 2',3'-didehydro-2',3'-dideoxythymidine (CAS REGISTRY NUMBERS: 3056-17-5: d4T: stavudine), 3'-thia-2',3'-dideoxycytidine (CAS REGISTRY NUMBERS: 134678-17-4: 3TC: lamivudine), 2'-β-fluoro-ddC, 3'-fluorothymidine (CAS REGISTRY NUMBERS: 25526-93-6: FLT), 9-(2-phosphonyl-methoxyethyl)-adenine (CAS REGISTRY NUMBERS: 106941-25-7: PMEA), 6-Cl-ddI, 6-Cl-ddC, and the like.

Also, as the non-nucleoside type inhibitors, there may be mentioned, for example, tetrahydro-imidazo-benzo-diazepin-one or -thione (TIBO) derivative (more specifically, (+)-S-4,5,6,7-tetrahydro-5-methyl-6-(3-methyl-2-butenyl)imidazo[4,5,1-jk][1,4]benzodiazepin-2(1H)-thione) (CAS REGISTRY NUMBERS: 167206-29-3: R82913), hydroxyethoxy-methylphenylthiothymine (HEPT) derivative, Nevirapine (CAS REGISTRY NUMBERS: 129618-40-2), pyridinone derivative, and the like.

In consideration of easiness of binding to the above-mentioned polypeptide and an effective inhibition mechanism of DNA synthesis by being taken into DNA, a nucleoside type reverse transcriptase inhibitor is preferred among these, and among the nucleoside type HIV reverse transcriptase inhibitors, preferred are AZT, ddI, ddC, d4T or 3TC which have already been administered to human clinically, and more preferred is AZT in which antiviral activity thereof is particularly and synergistically strengthened when it is chemically bonded to said polypeptide to form a substance of the present invention. These nucleoside type reverse transcriptase inhibitors, etc. are taken into DNA when HIV synthesizes DNA from RNA by reverse transcription, and as a result, it inhibits synthesis of DNA, therefore, a unnatural type nucleoside or nucleoside analogue is preferred. The above-mentioned nucleoside analogue means a non-nucleoside compound having a similar stereostructure to that of the nucleoside. Also, as these reverse transcriptase inhibitors, those commercially available or prepared according to the known synthetic method can be used.

Further, as the HIV protease inhibitor, it is a substance which inhibits an activity of protease of HIV, and preferably an inhibitor which is a substrate transition-state mimic compound of said protease. The substrate transition-state mimic compound means a substance capable of binding to a substrate binding domain of an enzyme and a substance having a similar stereostructure as that of a substrate in an enzyme-substrate complex. There may be mentioned, for example, Ro 31-8959 (CAS REGISTRY NUMBERS: 127779-20-8: saquinavir), A-77003 (CAS REGISTRY NUMBERS: 134878-17-4), A-80987 (CAS REGISTRY NUMBERS: 144141-97-9), KNI-93 (CAS REGISTRY NUMBERS: 138258-64-7), KNI-102 (CAS REGISTRY NUMBERS: 139694-65-8), KNI-174, KNI-227 (CAS REGISTRY NUMBERS: 147384-69-8), KNI-272 (CAS REGISTRY NUMBERS: 147318-81-8), L-735527 (CAS REGISTRY NUMBERS: 150378-17-9: indinavir), SC-52151 (CAS REGISTRY NUMBERS: 143224-34-4: Telinavir), VX-478, ABT-538 (CAS REGISTRY NUMBERS: 155213-67-5: ritonavir), DMP-323 (CAS REGISTRY NUMBERS: 151867-81-1), U-96988 (CAS REGISTRY NUMBERS: 149394-65-0), and the like. More preferably, Ro 31-8959, L-735527 and KN-272 having high antiviral activity are preferred but it is not specifically limited. As these HIV protease inhibitors, those commercially available or prepared according to the known synthetic method can be used. With regard to Ro 31-8959, there may be mentioned, for example, a preparation method described in J. Med. Chem. 36, p. 2300-2310 (1993).

In the above-mentioned complex, the above-mentioned polypeptide and the above-mentioned anti-HIV activity substance are chemically bonded, and the bond is not specifically limited so long as the bond is chemically formed. Specifically, there may be mentioned an ester bond, amide bond, ether bond, disulfide bond, etc. Of these, the ester bond is a bond capable of being cleaved by an intracellular esterase, etc. after the bonded anti-HIV activity substance is transferred to a target cell in vivo, so that said anti-HIV activity substance is released at a proximity of an action site of the anti-HIV activity substance, and the bond having a stability to an extent which is not easily cleaved in the course of transfer to the target cell. Accordingly, the ester bond is most preferred.

As a preparation method of the above-mentioned complex, for example, it is possible to prepare a complex of the polypeptide and the anti-HIV substance such as AZT, etc., by forming a bond between the amino terminus or the carboxy terminus of the polypeptide and the above-mentioned anti-HIV substance in an organic solvent such as pyridine, etc. For preparing such a complex, a spacer such as succinic acid or glutaric acid, etc. can be used between the polypeptide and the anti-HIV substance. In such a case, for example, an acid anhydride of succinic acid or glutaric acid is used and these carboxylic acids form an ester bond with the anti-HIV substance such as AZT, etc. in the presence of dimethylaminopyridine, and then, the resulting complex and an $\alpha$-amino group or $\omega$-amino group of the N-terminal amino acid of the polypeptide which is bound to the above-mentioned resin can be linked. It is also possible to prepare a material, in advance, in which a dendrite spacer (for example, polylysine, etc.) is linked to an arginine residue at the amino terminus of the polypeptide according to the present invention, and then, to condense the material by a conventionally known method (for example, DIPCI-HOBt method) to link them.

Incidentally, according to the same method as the linking process of the above-mentioned anti-HIV substance, it is also possible to elongate a half-life of the substance according to the present invention in vivo by linking, to the substance of the present invention, an in vivo half-life elongation substance such as polyethylene glycol (U.S. Pat. No. 5,342,940, etc.) or its derivative, glycosaminoglycan (U.S. Pat. No. 5,310,881, U.S. Pat. No. 4,585,754, etc.) such as chondroitin, etc., lipids such as lecithin (U.S. Pat. No. 5,109,118, No. 5,310,958, No. 5,362,491, etc.), etc., or styrene derivative polymer (Polym. J., 17:567, 1985, etc.) to which various kinds of oligosaccharides are bound, etc.

The polypeptide thus obtained can be isolated and purified by an isolation and purification means of a polypeptide which are conventionally known per se., such as extraction, recrystallization, various kinds of chromatographies (gel filtration, ion-exchange, distribution, adsorption, reverse phase), electrophoresis, counter current distribution, etc., particularly a method by reverse phase high performance liquid chromatography is most effective.

Also, the thus obtained polypeptide is considered to have endotoxin binding ability, antibacterial activity, endotoxin-sensitized hematocyte hemolysis and antiviral activity as in the conventionally known polypeptide derived from horseshoe crab, T134 and T140, and it was shown to have particularly good antiviral activity to human immunodeficiency virus (HIV), and its cytotoxicity is markedly reduced as compared to the conventional T134 and T140.

The polypeptide represented by the formula (I) according to the present invention shows basic property due to the characteristic feature of the amino acids constituting it, therefore, it may be in the form of a salt formed by acid addition. For example, the polypeptide represented by the formula (I) forms a salt with an inorganic acid (hydrochloric acid, hydrobromic acid, phosphoric acid, nitric acid, sulfuric acid, etc.), an organic carboxylic acid (acetic acid, propionic acid, maleic acid, succinic acid, malic acid, citric acid, tartaric acid, salicylic acid, etc.) or an organic sulfonic acid (methanesulfonic acid, p-toluenesulfonic acid, etc.). The polypeptide represented by the formula (I) according to the present invention can be used as an effective ingredient of a medical composition as a pharmaceutically acceptable salt.

Incidentally, the polypeptide of the formula (I) has a function of specifically binding to a CXCR4 ligand, and according to this specificity, it can be considered to have an anti-HIV virus activity. It can be also considered, in addition to anti-HIV virus agent, to utilize the same as a medical composition for treatment of cancer, acute lymphoma, osterosarcoma, heterotopia osteogenesis, rheumatism, etc., which are diseases in which a CXCR4 ligand is involved.

EXAMPLE

<Preparation of Polypeptide>

Preparation of polypeptide TC14005 (SEQ ID NO: 13) H-Arg-Arg-Nal-Cys-Tyr-Arg-Lys-DCit-Pro-Tyr-Arg-Cit-Cys-Arg-OH (TC14005)

1. Synthesis of Protected Polypeptide TC14005 Resin

After a Fmoc group was removed by 20% piperidine/DMF, from 270 mg (0.2 mmol) of Fmoc-Arg(Pbf)-OH (0.74 mg/g) of Alko resin to which arginine had been introduced at the 14-position (which is the 13-position of the formula (I)) Fmoc-Cys (Trt)-OH (2.5 eq) which corresponds to the 13-position (which is the 12-position of the formula (I)) was added to the Alko resin, and a condensation reaction was carried out by the DIPCDI-HOBt method in DMF. A degree of progress of the condensation reaction was examined by a ninhydrin test of Kaiser. E et al. (Anal. Biochem., 34:595 (1970)).

2. Introduction of Amino Acids at 12-Position to 1-Position

In the same manner as mentioned above, Cit, Arg(Pbf), Tyr(t-Bu), Pro, D-Cit, Lys(Boc), Arg(Pbf), Tyr(t-Bu), Cys (Trt), Nal, Arg(Pbf) and Arg(Pbf) residues were successsively introduced to the DMBHA resin to obtain a functionl group-protected polypeptide (I) resin.

3. Deprotection of the Protecting Groups, Separation and Purification of the Polypeptide from Resin A Fmoc group was removed from the functional group-protected polypeptide (1) resin by 20% piperidine/DMF treatment, and then, the resin was reacted in 1M-TMSBr-thioanisol/TFA (trifluoroacetic acid) system (10 ml of trifluoroacetic acid containing m-cresol (100 eq) and ethanedithiol (300 eq)) per 100 mg of the resin at 25° C. for 2 hours. The resin was collected by filtration from the reaction mixture, and washed twice with 1 ml of trifluoroacetic acid, 100 ml of ice-cooled dry ether was added to the combined solution of the filtrate and the washed solution, formed precipitates were separated by centrifugation, and the residue was separated from a supernatant by decantation. The obtained residue was washed with cooled ether, and dissolved in 10 ml of 4N acetic acid, 830 mg (80 eq) of dithiothreitol was added to the solution, and the resulting mixed solution was stirred overnight. The reaction mixture was centrifuged, the supernatant was treated by Sephadex G-10 (available from Pharmacia Co.: 3.7×50 cm), and subjected to gel filtration with 4N acetic acid, and a main eluted portion which was a passed through fraction were collected, and lyophilized to obtain powder state partially purified uncyclized polypeptide TC14005.

4. Cyclization by Air Oxidation

A half amount of the above-mentioned polypeptide was adjusted to pH 7.5 with conc. aqueous ammonia, and air oxidation was carried out by passing air through the mixture to carry out cyclization. After completion of the air oxidation, the cyclized polypeptide was adsorbed to 10 g of DIAION HP-20 resin (available from Mitsubishi Chemical Co., Ltd.), and then, subjected to desorption and elution by using 60% acetonitrile (in 1N acetic acid). Said eluent was concentrated under reduced pressure at room temperature to remove acetonitrile, and further lyophilized to make powder. Further, said powder was dissolved in water, and purified by HPLC (Cosmodule 5C18ARII column: acetonitrile gradient elution) to obtain a polypeptide with a single peak. Purity thereof was confirmed by HPLC.

$[\alpha]D$ (c. 0.1: $H_2O$): +42.73

Ion spray mass spectrum (IS-MS): ($C_{90}H_{140}N_{34}O_{19}S_2$) Calculated value: 2066.43, Measured value: 2067

(triple-stage quadrupole mass spectrum analyzer APIII (Perkin-Elmer Scie X)

Preparation of polypeptide TC14012 (SEQ ID NO: 15) H-Arg-Arg-Nal-Cys-Tyr-Cit-Lys-DCit-Pro-Tyr-Arg-Cit-Cys-Arg-$NH_2$ (TC14012)

1. Synthesis of Protected Polypeptide TC14012 Resin

After a Fmoc group of 1.47 g (1 mmole) of Fmoc-NH-SAL resin (0.68 mmole/g) was removed by 20% piperidine/DMF, Fmoc-Arg(Pbf)-OH (2.5 eq) which corresponds to the 14-position was added to the NH-SAL resin and the resulting mixture was subjected to condensation reaction by DIPCDI-HOBt.

2. Introduction of Amino Acids at 13-Position to 1-Position

In the same manner as mentioned above, Cys(Trt), Cit, Arg(Pbf), Tyr(t-Bu), Pro, D-Cit, Lys(Boc), Cit, Tyr(t-Bu), Cys(Trt), Nal, Arg(Pbf), Arg(Pbf) residues were successively introduced to the NH-SAL resin to obtain a functional group-protected polypeptide resin.

Thereafter, in the same manner as in the synthesis of TC14005, deprotection of the protecting group, separation and purification of the polypeptide from the resin were carried out and cyclization was carried out by air oxidation to obtain TC14012.

Yielded amount: 1.432 g (Yield: 59%)

$[\alpha]D$(c 0.41: $H_2O$): −60.67

Ion spray mass spectrum (IS-MS): ($C_{90}H_{140}N_{34}O_{19}S_2$) Calculated value: 2066.43, Measured value: 2065.73

(triple-stage quadrupole mass spectrum analyzer APIII (Perkin-Elmer Scie X)

In the same manner as mentioned above, other polypeptides of the present invention shown in Table 1 were synthesized and their IS-MS results are shown in the following Table 2.

|  | Formula | IS-MS (Calculated value) | IS-MS (Mearured value) |
|---|---|---|---|
| TA14001 | $C_{87}H_{134}N_{30}O_{18}S_2$ | 1952.33 | 1952 |
| TA14005 | $C_{87}H_{134}N_{30}O_{18}S_2$ | 1952.33 | 1953 |
| TA14006 | $C_{87}H_{134}N_{32}O_{18}S_2$ | 1980.34 | 1981 |
| TA14007 | $C_{87}H_{134}N_{32}O_{18}S_2$ | 1980.34 | 1981 |
| TA14008 | $C_{87}H_{139}N_{33}O_{18}S_2$ | 2011.40 | 2012 |
| TA14009 | $C_{84}H_{137}N_{33}O_{17}S_2$ | 1945.34 | 1948 |
| TA14010 | $C_{87}H_{134}N_{30}O_{18}S_2$ | 1952.33 | 1953 |
| TC14001 | $C_{90}H_{140}N_{32}O_{19}S_2$ | 2038.42 | 2039 |
| TC14003 | $C_{90}H_{140}N_{32}O_{19}S_2$ | 2038.42 | 2038 |
| TC14004 | $C_{90}H_{140}N_{34}O_{19}S_2$ | 2066.43 | 2067 |
| TC14006 | $C_{90}H_{140}N_{32}O_{19}S_2$ | 2038.42 | 2037 |
| TC14011 | $C_{90}H_{139}N_{33}O_{20}S_2$ | 2067.42 | 2068 |
| TC14018 | $C_{90}H_{140}N_{34}O_{19}S_2$ | 2066.43 | 2066 |
| TC14020 | $C_{90}H_{140}N_{34}O_{19}S_2$ | 2066.43 | 2066 |
| TN14003 | $C_{90}H_{141}N_{33}O_{18}S_2$ | 2037.43 | 2038 |
| TN14005 | $C_{90}H_{141}N_{35}O_{18}S_2$ | 2065.45 | 2066 |

Incidentally, as an optical rotation, the following values were obtained.

TC14003: $[\alpha]D$(c. 0.1: $H_2O$): 0
TC14011: $[\alpha]D$(c. 0.1: $H_2O$): −47.61
TC14018: $[\alpha]D$(c. 0.1: $H_2O$): −25.51
TC14020: $[\alpha]D$(c. 0.1: $H_2O$): −41.74
TN14003: $[\alpha]D$(c. 0.1: $H_2O$): −37.09
TN14005: $[\alpha]D$(c. 0.1: $H_2O$): −27.58

CD spectra of the polypeptide TC14003 and TC14005 according to the present invention were measured. By using J-720 spectropolarimeter (manufactured by JASCO Co.) and using 1 cm cell, samples were measured with a distance of 1 nm five times, and an average value of the 5 times was obtained, and the results are shown in FIG. 1 with the CD spectra of the conventional T140. Minus peak at around 210 nm and plus peak at around 197 nm were observed, so that it was clarified that these peptides have β-sheet structure.

<Anti-HIV Activity and Cytotoxicity>

HIV-1 (IIIB) strain obtained from MOLT/HIV-1 (IIIB) cell previously infected by HIV-1 was used. The poly-peptide of the present invention was added to MT-4 cell infected by HIV in various kinds of concentrations, and a number of living cells after culturing at 37° C. for 5 days was determined by using a 3'-(4,5-dimethylthiazol-2-yl)-2,5-diphenyltetrazolinium bromide (MTT) method. Anti-HIV activity is shown by a concentration ($EC_{50}$ value), where MT-4 cell death by HIV infection is inhibited by 50%. Cytotoxicity of the peptide according to the present invention was shown by a 50% survival concentration (Test I: $CC_{50}$ value) by culturing virus-uninfected MT-4 cells with the polypeptide according to the present invention in various concentrations, and determining a number of living cells by the MTT method. Moreover, a number of living cells of human peripheral blood monocyte (PBMC) was determined by trypan blue dyeing method, and shown by a 50% survival concentration (Test II: $CC_{50}$ value). Respective ratios of the $CC_{50}$ value and the $EC_{50}$ value were shown as an selective index (SI). Obtained values were summarized in the table using the conventionally known polypeptides T134 and T140, and an anti-HIV compound: 3'-azido-2',3'-dideoxythymidine (AZT) used as a medicine as a control anti-HIV agent.

| Compound | Charge | $EC_{50}$ (nM) | $CC_{50}$ (μM) (Test I) | $CC_{50}$ (μM) (Test II) | SI $CC_{50}$ (Test I)/$EC_{50}$ | SI $CC_{50}$ (Test II)/$EC_{50}$ |
|---|---|---|---|---|---|---|
| T134 | 7 | 8.3 | >>1 | 190 | >>120 | 23000 |
| T140 | 7 | 3.3 | >>1 | 96 | >>300 | 29000 |
| TA14001 | 6 | 56 | >40 | N.T. | >750 | N.T. |
| TA14005 | 6 | 9.3 | >40 | N.T. | >4500 | N.T. |
| TA14006 | 6 | 47 | >80 | N.T. | >1800 | N.T. |
| TA14007 | 6 | 16 | >80 | N.T. | >5200 | N.T. |

-continued

| Compound | Charge | EC$_{50}$ (nM) | CC$_{50}$ (μM) (Test I) | CC$_{50}$ (μM) (Test II) | SI CC$_{50}$ (Test I)/EC$_{50}$ | CC$_{50}$ (Test II)/EC$_{50}$ |
|---|---|---|---|---|---|---|
| TA14008 | 7 | 17 | >80 | N.T. | >4700 | N.T. |
| TA14009 | 7 | 17 | >80 | N.T. | >4500 | N.T. |
| TA14010 | 6 | 18 | >80 | N.T. | >4800 | N.T. |
| TC14003 | 6 | 2.8 | >80 | 310 | >29000 | 160000 |
| TC14004 | 6 | 16 | >80 | 270 | >5000 | 16000 |
| TC14005 | 6 | 4.0 | >80 | 280 | >20000 | 69000 |
| TC14006 | 6 | 15 | >80 | 310 | >5300 | 20000 |
| TC14011 | 5 | 0.5 | >100 | N.T. | >200000 | N.T. |
| TC14012 | 6 | 0.4 | >100 | N.T. | >250000 | N.T. |
| TC14018 | 6 | 1.2 | >100 | N.T. | >83000 | N.T. |
| TC14020 | 6 | 2.7 | >100 | N.T. | >37000 | N.T. |
| TN14003 | 6 | 0.6 | >100 | N.T. | >166000 | N.T. |
| TN14005 | 6 | 4.6 | >100 | N.T. | >21000 | N.T. |
| AZT | | 48 | 190 | <20 | 4000 | <410 |

Charge is a number of total positive charges of the respective peptides; all the values are an average of measured values taken at least three times; and NT shows that no test was carried out.

From the above-mentioned table, it is clear that the compounds of the present invention, particularly TC14003, TC14005, TC14020 and TN14005 have substantially the same anti-HIV activity as that of the conventionally known T140, and cytotoxicity is markedly lowered. Moreover, it is clear that TC14011, TC14012, TC14018, TC14020 and TN14003 have higher anti-HIV activity in addition to lowered cytotoxicity.

<Stability in Sera>

Figure 2:
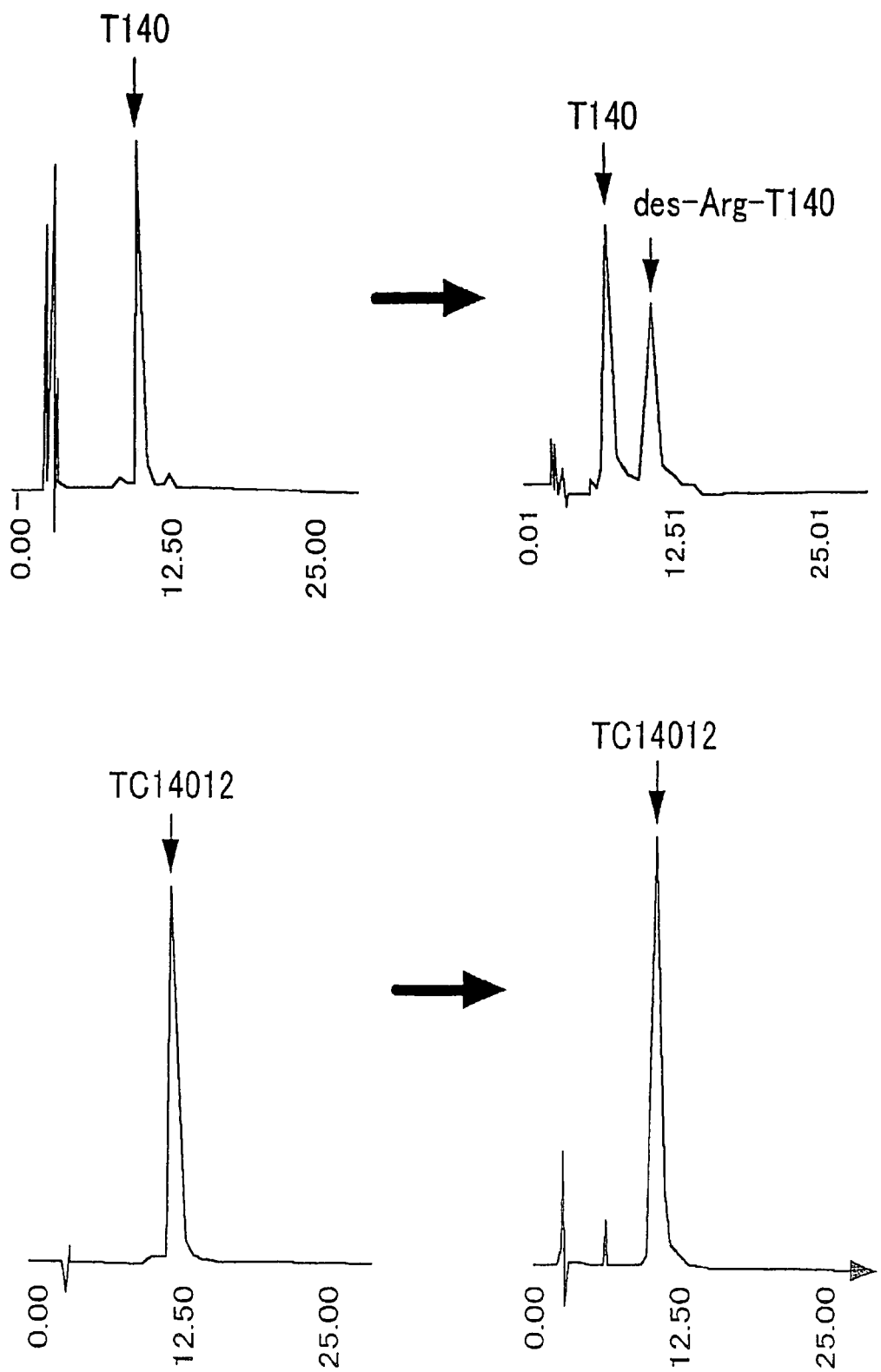
FIG. 2 is a HPLC chart showing stabilities of poly-peptides TC14012 of the present invention and T140 in serum.

T140 or TC14012 was dissolved in cat serum (100 μL/100 μL Water) in an amount of 100 nmol, and maintained at 37° C. Each 8 μL of the respective samples were collected after 0 hour, 1 hour, 2 hours, 5 hours and 16 hours, and analyzed by reverse phase HPLC using 16% acetonitrile. As a result, in the case of T140, about 70% was decomposed after 16 hours, but substantially no decomposition was observed in TC14012 (FIG. 2).

This shows that the carboxyl terminus of the poly-peptide according to the present invention is amidated, then stability of the polypeptide in serum is remarkably improved.

Sequence Listing Free Text

SEQ. ID. NO: 1: Designed peptide based on tachyplesin family polypeptide of horseshoe crab, 8Xaa: D-Lys, 12Xaa: L-citrulline SEQ. ID. NO: 2: Designed peptide based on tachyplesin family polypeptide of horseshoe crab, 3Xaa: L-3-(2-naphthyl)alanine, 8Xaa: D-Lys, 12Xaa: L-citrulline SEQ. ID. NO: 3: Designed peptide based on tachyplesin family polypeptide of horseshoe crab, 3Xaa: L-3-(2-naphthyl)alanine, 8Xaa: D-Lys, 12Xaa: L-citrulline SEQ. ID. NO: 4: Designed peptide based on tachyplesin family polypeptide of horseshoe crab, 3Xaa: L-3-(2-naphthyl)alanine, 8Xaa: D-Lys, 12Xaa: L-citrulline SEQ. ID. NO: 5: Designed peptide based on tachyplesin family polypeptide of horseshoe crab, 3Xaa: L-3-(2-naphthyl)alanine, 8Xaa: D-Lys, 12Xaa: L-citrulline SEQ. ID. NO: 6: Designed peptide based on tachyplesin family polypeptide of horseshoe crab, 3Xaa: L-3-(2-naphthyl)alanine, 8Xaa: D-Lys, 12Xaa: L-citrulline SEQ. ID. NO: 7: Designed peptide based on tachyplesin family polypeptide of horseshoe crab, 3Xaa: L-3-(2-naphthyl)alanine, 8Xaa: D-Lys, 12Xaa: L-citrulline SEQ. ID. NO: 8: Designed peptide based on tachyplesin family polypeptide of horseshoe crab, 3Xaa: L-3-(2-naphthyl)alanine, 8Xaa: D-Lys, 12Xaa: L-citrulline SEQ. ID. NO: 9: Designed peptide based on tachyplesin family polypeptide of horseshoe crab, 3Xaa: L-3-(2-naphthyl)alanine, 8Xaa: D-Lys, 12Xaa: L-citrulline SEQ. ID. NO: 10: Designed peptide based on tachyplesin family polypeptide of horseshoe crab, 1Xaa: L-citrulline, 3Xaa: L-3-(2-naphthyl)alanine, 8Xaa: D-Lys, 12Xaa: L-citrulline SEQ. ID. NO: 11: Designed peptide based on tachyplesin family polypeptide of horseshoe crab, 3Xaa: L-3-(2-naphthyl)alanine, 6Xaa: L-citrulline, 8Xaa: D-Lys, 12Xaa: L-citrulline SEQ. ID. NO: 12: Designed peptide based on tachyplesin family polypeptide of horseshoe crab, 3Xaa: L-3-(2-naphthyl)alanine, 7Xaa: L-citrulline, 8Xaa: D-Lys, 12Xaa: L-citrulline SEQ. ID. NO: 13: Designed peptide based on tachyplesin family polypeptide of horseshoe crab, 3Xaa: L-3-(2-naphthyl)alanine, 8Xaa: D-citrulline, 12Xaa: L-citrulline SEQ. ID. NO: 14: Designed peptide based on tachyplesin family polypeptide of horseshoe crab, 3Xaa: L-3-(2-naphthyl)alanine, 8Xaa: D-Lys, 11Xaa: L-citrulline, 12Xaa: L-citrulline SEQ. ID. NO: 15: Designed peptide based on tachyplesin family polypeptide of horseshoe crab, 3Xaa: L-3-(2-naphthyl)alanine, 6Xaa: L-citrulline, D-citrulline, 12Xaa: L-citrulline SEQ. ID. NO: 16: Designed peptide based on tachyplesin family polypeptide of horseshoe crab, 1Xaa: L-citrulline, 3Xaa: L-3-(2-naphthyl)alanine, 8Xaa: D-citrulline, 12Xaa: L-citrulline SEQ. ID. NO: 17: Designed peptide based on tachyplesin family polypeptide of horseshoe crab, 3Xaa: L-3-(2-naphthyl)alanine, 8Xaa: D-citrulline, 11Xaa: L-citrulline, 12Xaa: L-citrulline

UTILIZABILITY IN INDUSTRY

According to the present invention, novel polypeptides having low cytotoxicity and high anti-HIV activity can be provided.

SEQUENCE LISTING

<160> NUMBER OF SEQ ID NOS: 28

<210> SEQ ID NO 1
<211> LENGTH: 14
<212> TYPE: PRT
<213> ORGANISM: Artificial Sequence
<220> FEATURE:

```
<223> OTHER INFORMATION: Designed peptide based on tachyplesin family
      polypeptide of horseshoe crab
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (12)
<223> OTHER INFORMATION: L-citrulline

<400> SEQUENCE: 1

Arg Arg Trp Cys Tyr Arg Lys Xaa Pro Tyr Arg Xaa Cys Arg
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (12)
<223> OTHER INFORMATION: L-citrulline

<400> SEQUENCE: 2

Arg Arg Xaa Cys Tyr Arg Lys Xaa Pro Tyr Arg Xaa Cys Arg
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (12)
<223> OTHER INFORMATION: L-citrulline

<400> SEQUENCE: 3

Ala Arg Xaa Cys Tyr Arg Lys Xaa Pro Tyr Arg Xaa Cys Arg
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)
```

```
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (12)
<223> OTHER INFORMATION: L-citrulline

<400> SEQUENCE: 4

Arg Arg Xaa Cys Tyr Ala Lys Xaa Pro Tyr Arg Xaa Cys Arg
 1               5                  10

<210> SEQ ID NO 5
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (12)
<223> OTHER INFORMATION: L-citrulline

<400> SEQUENCE: 5

Arg Arg Xaa Cys Tyr Arg Ala Xaa Pro Tyr Arg Xaa Cys Arg
 1               5                  10

<210> SEQ ID NO 6
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-Ala
<220> FEATURE:
<221> NAME/KEY: MOD_RES
<222> LOCATION: (12)
<223> OTHER INFORMATION: L-citrulline

<400> SEQUENCE: 6

Arg Arg Xaa Cys Tyr Arg Lys Xaa Pro Tyr Arg Xaa Cys Arg
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)
<223> OTHER INFORMATION: L-3-(2-Naphthyl)alanine
```

```
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (12)
<223> OTHER INFORMATION: L-citrulline

<400> SEQUENCE: 7

Arg Arg Xaa Cys Tyr Arg Lys Xaa Ala Tyr Arg Xaa Cys Arg
 1               5                  10

<210> SEQ ID NO 8
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (12)
<223> OTHER INFORMATION: L-citrulline

<400> SEQUENCE: 8

Arg Arg Xaa Cys Tyr Arg Lys Xaa Pro Ala Arg Xaa Cys Arg
 1               5                  10

<210> SEQ ID NO 9
<211> LENGTH: 14
<212> TYPE: PRT
<213> ORGANISM: Artificial Sequence
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (12)
<223> OTHER INFORMATION: L-citrulline
<220> FEATURE:
<223> OTHER INFORMATION: Designed peptide based on tachyplesin family
      polypeptide of horseshoe crab

<400> SEQUENCE: 9

Arg Arg Xaa Cys Tyr Arg Lys Xaa Pro Tyr Ala Xaa Cys Arg
 1               5                  10

<210> SEQ ID NO 10
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (1)
<223> OTHER INFORMATION: L-citrulline
<220> FEATURE:
```

```
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (12)
<223> OTHER INFORMATION: L-citrulline

<400> SEQUENCE: 10

Xaa Arg Xaa Cys Tyr Arg Lys Xaa Pro Tyr Arg Xaa Cys Arg
 1               5                  10

<210> SEQ ID NO 11
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: misc_feature
<223> OTHER INFORMATION: C' Amidated peptide
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (6)
<223> OTHER INFORMATION: L-citrulline
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (12)
<223> OTHER INFORMATION: L-citrulline

<400> SEQUENCE: 11

Arg Arg Xaa Cys Tyr Xaa Lys Xaa Pro Tyr Arg Xaa Cys Arg
 1               5                  10

<210> SEQ ID NO 12
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (7)
<223> OTHER INFORMATION: L-citrulline
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (12)
<223> OTHER INFORMATION: L-citrulline

<400> SEQUENCE: 12

Arg Arg Xaa Cys Tyr Arg Xaa Xaa Pro Tyr Arg Xaa Cys Arg
 1               5                  10
```

```
<210> SEQ ID NO 13
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: misc_feature
<223> OTHER INFORMATION: C' Amidated peptide
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-citrulline
<220> FEATURE:
<221> NAME/KEY: MOD_RES
<222> LOCATION: (12)
<223> OTHER INFORMATION: L-citrulline

<400> SEQUENCE: 13

Arg Arg Xaa Cys Tyr Arg Lys Xaa Pro Tyr Arg Xaa Cys Arg
 1               5                  10

<210> SEQ ID NO 14
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-Lys
<220> FEATURE:
<221> NAME/KEY: MOD_RES
<222> LOCATION: (11)..(12)
<223> OTHER INFORMATION: L-citrulline

<400> SEQUENCE: 14

Arg Arg Xaa Cys Tyr Arg Lys Xaa Pro Tyr Xaa Xaa Cys Arg
 1               5                  10

<210> SEQ ID NO 15
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: misc_feature
<223> OTHER INFORMATION: C' Amidated peptide
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (6)
<223> OTHER INFORMATION: L-citrulline
<220> FEATURE:
<221> NAME/KEY: MOD_RES
<222> LOCATION: (8)
<223> OTHER INFORMATION: D-citrulline
```

```
<220> FEATURE:
<221> NAME/KEY: MOD_RES
<222> LOCATION: (12)
<223> OTHER INFORMATION: L-citrulline

<400> SEQUENCE: 15

Arg Arg Xaa Cys Tyr Xaa Lys Xaa Pro Tyr Arg Xaa Cys Arg
 1               5                  10

<210> SEQ ID NO 16
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: misc_feature
<223> OTHER INFORMATION: C' Amidated peptide
<220> FEATURE:
<221> NAME/KEY: MOD_RES
<222> LOCATION: (1)
<223> OTHER INFORMATION: L-citrulline
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-citrulline
<220> FEATURE:
<221> NAME/KEY: MOD_RES
<222> LOCATION: (12)
<223> OTHER INFORMATION: L-citrulline

<400> SEQUENCE: 16

Xaa Arg Xaa Cys Tyr Arg Lys Xaa Pro Tyr Arg Xaa Cys Arg
 1               5                  10

<210> SEQ ID NO 17
<211> LENGTH: 14
<212> TYPE: PRT
<213> ORGANISM: Artificial Sequence
<220> FEATURE:
<223> OTHER INFORMATION: Designed peptide based on tachyplesin family
      polypeptide of horseshoe crab
<220> FEATURE:
<221> NAME/KEY: MOD_RES
<222> LOCATION: (3)
<223> OTHER INFORMATION: L-3-(2-Naphthyl)alanine
<220> FEATURE:
<221> NAME/KEY: MOD_RES
<222> LOCATION: (8)
<223> OTHER INFORMATION: D-citrulline
<220> FEATURE:
<221> NAME/KEY: MOD_RES
<222> LOCATION: (11)..(12)
<223> OTHER INFORMATION: L-citrulline

<400> SEQUENCE: 17

Arg Arg Xaa Cys Tyr Arg Lys Xaa Pro Tyr Xaa Xaa Cys Arg
 1               5                  10

<210> SEQ ID NO 18
<211> LENGTH: 18
<212> TYPE: PRT
<213> ORGANISM: Artificial Sequence
<220> FEATURE:
<223> OTHER INFORMATION: Formula peptide
<220> FEATURE:
<221> NAME/KEY: MOD_RES
<222> LOCATION: (1)
```

```
<223> OTHER INFORMATION: Arg, Lys, Ala, ornithine, citrulline, any
      derivative of these amino acids, or not present
<220> FEATURE:
<221> NAME/KEY: MOD_RES
<222> LOCATION: (3)
<223> OTHER INFORMATION: Any aromatic amino acid
<220> FEATURE:
<221> NAME/KEY: MOD_RES
<222> LOCATION: (6)..(7)
<223> OTHER INFORMATION: Arg, Lys, Ala, ornithine or citrulline
<220> FEATURE:
<221> NAME/KEY: MOD_RES
<222> LOCATION: (8)
<223> OTHER INFORMATION: Ala, Val, Leu, Ile, Ser, Cys or Met
<220> FEATURE:
<221> NAME/KEY: MOD_RES
<222> LOCATION: (9)
<223> OTHER INFORMATION: Any aromatic amino acid
<220> FEATURE:
<221> NAME/KEY: MOD_RES
<222> LOCATION: (10)
<223> OTHER INFORMATION: Arg, Lys, Ala, ornithine or citrulline
<220> FEATURE:
<221> NAME/KEY: MOD_RES
<222> LOCATION: (12)
<223> OTHER INFORMATION: Tyr, Phe, Trp, Ala, Val, Leu, Ile, Ser, Cys or
      Met; see specification as filed for detailed description of
      substitutions and preferred embodiments
<220> FEATURE:
<221> NAME/KEY: DISULFID
<222> LOCATION: (8)..(13)
<223> OTHER INFORMATION: when positions 8 and 13 are Cys, they may form
      a disulfide bond
<220> FEATURE:
<221> NAME/KEY: DISULFID
<222> LOCATION: (4)..(12)
<223> OTHER INFORMATION: when position 12 is Cys, a disulfide bond may
      be formed with the Cys at position 4
<220> FEATURE:
<221> NAME/KEY: MISC_FEATURE
<222> LOCATION: (8)..(13)
<223> OTHER INFORMATION: according to the specification as filed, this
      range may be encompassed by a single residue containing a
      D-citrulline, D-Ala, citrulline or Ala
<220> FEATURE:
<221> NAME/KEY: MOD_RES
<222> LOCATION: (13)
<223> OTHER INFORMATION: Ala, Val, Leu, Ile, Ser, Cys or Met
<220> FEATURE:
<221> NAME/KEY: MOD_RES
<222> LOCATION: (14)
<223> OTHER INFORMATION: Tyr, Phe, Ala, naphthylalanine or citrulline
<220> FEATURE:
<221> NAME/KEY: MOD_RES
<222> LOCATION: (15)
<223> OTHER INFORMATION: Arg, Lys, Ala, ornithine or citrulline
<220> FEATURE:
<221> NAME/KEY: MOD_RES
<222> LOCATION: (16)
<223> OTHER INFORMATION: citrulline
<220> FEATURE:
<221> NAME/KEY: MOD_RES
<222> LOCATION: (18)
<223> OTHER INFORMATION: Lys or Arg; a carboxyl group may be amidated
<220> FEATURE:
<221> NAME/KEY: MISC_FEATURE
<222> LOCATION: (1)..(18)
<223> OTHER INFORMATION: this sequence is structured with the proviso
      that either of the amino acid residues at positions 1, 6, 7, 14,
      15 and 18 is Ala or citrulline or that the single amino acid that
      may be present at position 8 is D-citrulline, citrulline, D-Ala or
      Ala
<220> FEATURE:
<223> OTHER INFORMATION: see specification as filed for detailed
      description of substitutions and preferred embodiments

<400> SEQUENCE: 18

Xaa Arg Xaa Cys Tyr Xaa Xaa Xaa Xaa Xaa Gly Xaa Xaa Xaa Xaa Xaa
```

Cys Xaa

<210> SEQ ID NO 19
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Citrulline
<220> FEATURE:
<221> NAME/KEY: misc_feature
<222> LOCATION: (3)..(3)
<223> OTHER INFORMATION: Naphthylalanine
<220> FEATURE:
<221> NAME/KEY: misc_feature
<222> LOCATION: (6)..(6)
<223> OTHER INFORMATION: Citrulline
<220> FEATURE:
<221> NAME/KEY: misc_feature
<222> LOCATION: (8)..(8)
<223> OTHER INFORMATION: D stereo isomer
<220> FEATURE:
<221> NAME/KEY: misc_feature
<222> LOCATION: (12)..(12)
<223> OTHER INFORMATION: L-Citrulline

<400> SEQUENCE: 19

Xaa Arg Xaa Cys Tyr Xaa Lys Lys Pro Tyr Arg Xaa Cys Arg
1               5                   10

<210> SEQ ID NO 20
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Naphthylalanine
<220> FEATURE:
<221> NAME/KEY: misc_feature
<222> LOCATION: (6)..(6)
<223> OTHER INFORMATION: L-citrulline
<220> FEATURE:
<221> NAME/KEY: misc_feature
<222> LOCATION: (8)..(8)
<223> OTHER INFORMATION: D stereo isomer
<220> FEATURE:
<221> NAME/KEY: misc_feature
<222> LOCATION: (12)..(12)
<223> OTHER INFORMATION: L-citrulline

<400> SEQUENCE: 20

Arg Arg Xaa Cys Tyr Xaa Lys Lys Pro Tyr Arg Xaa Cys Arg
1               5                   10

<210> SEQ ID NO 21
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Naphthylalanine
<220> FEATURE:
<221> NAME/KEY: misc_feature

```
<222> LOCATION: (8)..(8)
<223> OTHER INFORMATION: D-citrulline
<220> FEATURE:
<221> NAME/KEY: misc_feature
<222> LOCATION: (12)..(12)
<223> OTHER INFORMATION: L-citrulline

<400> SEQUENCE: 21

Arg Arg Xaa Cys Tyr Arg Lys Xaa Pro Tyr Arg Xaa Cys Arg
1               5                   10

<210> SEQ ID NO 22
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Naphthylalanine
<220> FEATURE:
<221> NAME/KEY: misc_feature
<222> LOCATION: (6)..(6)
<223> OTHER INFORMATION: L-citrulline
<220> FEATURE:
<221> NAME/KEY: misc_feature
<222> LOCATION: (8)..(8)
<223> OTHER INFORMATION: D-Citrulline
<220> FEATURE:
<221> NAME/KEY: misc_feature
<222> LOCATION: (12)..(12)
<223> OTHER INFORMATION: L-citrulline

<400> SEQUENCE: 22

Arg Arg Xaa Cys Tyr Xaa Lys Xaa Pro Tyr Arg Xaa Cys Arg
1               5                   10

<210> SEQ ID NO 23
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: arginine, alanine or citrulline residue
<220> FEATURE:
<221> NAME/KEY: misc_feature
<222> LOCATION: (3)..(3)
<223> OTHER INFORMATION: tryptophane or naphthylalanine residue
<220> FEATURE:
<221> NAME/KEY: misc_feature
<222> LOCATION: (6)..(6)
<223> OTHER INFORMATION: alanine or citrulline residue
<220> FEATURE:
<221> NAME/KEY: misc_feature
<222> LOCATION: (7)..(7)
<223> OTHER INFORMATION: lysine, alanine or citrulline residue
<220> FEATURE:
<221> NAME/KEY: misc_feature
<222> LOCATION: (8)..(9)
<223> OTHER INFORMATION: D-lysyl proline, D-alanyl proline, D-lysyl
     alanine or D-citrullyl proline residue
<220> FEATURE:
<221> NAME/KEY: misc_feature
<222> LOCATION: (10)..(10)
<223> OTHER INFORMATION: tyrosine or alanine residue
<220> FEATURE:
<221> NAME/KEY: misc_feature
<222> LOCATION: (11)..(11)
<223> OTHER INFORMATION: arginine, alanine or citrulline residue
<220> FEATURE:
<221> NAME/KEY: misc_feature
```

```
<222> LOCATION: (12)..(12)
<223> OTHER INFORMATION: citrulline

<400> SEQUENCE: 23

Xaa Arg Xaa Cys Tyr Xaa Xaa Xaa Xaa Xaa Xaa Xaa Cys Arg
1               5                   10

<210> SEQ ID NO 24
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)
<223> OTHER INFORMATION: Arg, Lys, Ala, ornithine, citrulline, any
      derivative of these amino acids, or not present
<220> FEATURE:
<221> NAME/KEY: MOD_RES
<222> LOCATION: (3)
<223> OTHER INFORMATION: naphthylalanine
<220> FEATURE:
<221> NAME/KEY: MOD_RES
<222> LOCATION: (6)
<223> OTHER INFORMATION: Arg, Lys, Ala, ornithine or citrulline
<220> FEATURE:
<221> NAME/KEY: MOD_RES
<222> LOCATION: (8)
<223> OTHER INFORMATION: Ala, Val, Leu, Ile, Ser, Cys or Met
<220> FEATURE:
<221> NAME/KEY: MOD_RES
<222> LOCATION: (9)
<223> OTHER INFORMATION: Any aromatic amino acid
<220> FEATURE:
<221> NAME/KEY: MOD_RES
<222> LOCATION: (10)
<223> OTHER INFORMATION: Arg, Lys, Ala, ornithine or citrulline
<220> FEATURE:
<221> NAME/KEY: MOD_RES
<222> LOCATION: (12)
<223> OTHER INFORMATION: Tyr, Phe, Trp, Ala, Val, Leu, Ile, Ser, Cys or
      Met; see specification as filed for detailed description of
      substitutions and preferred embodiments
<220> FEATURE:
<221> NAME/KEY: DISULFID
<222> LOCATION: (8)..(13)
<223> OTHER INFORMATION: when positions 8 and 13 are Cys, they may form
      a disulfide bond
<220> FEATURE:
<221> NAME/KEY: DISULFID
<222> LOCATION: (4)..(12)
<223> OTHER INFORMATION: when position 12 is Cys, a disulfide bond may
      be formed with the Cys at position 4
<220> FEATURE:
<221> NAME/KEY: MISC_FEATURE
<222> LOCATION: (8)..(13)
<223> OTHER INFORMATION: according to the specification as filed, this
      range may be encompassed by a single residue containing a
      D-citrulline, D-Ala, citrulline or Ala
<220> FEATURE:
<221> NAME/KEY: MOD_RES
<222> LOCATION: (13)
<223> OTHER INFORMATION: Ala, Val, Leu, Ile, Ser, Cys or Met
<220> FEATURE:
<221> NAME/KEY: MOD_RES
<222> LOCATION: (15)
<223> OTHER INFORMATION: Arg, Lys, Ala, ornithine or citrulline
<220> FEATURE:
<221> NAME/KEY: MOD_RES
<222> LOCATION: (16)
<223> OTHER INFORMATION: citrulline
<220> FEATURE:
<221> NAME/KEY: MISC_FEATURE
<222> LOCATION: (1)..(18)
<223> OTHER INFORMATION: this sequence is structured with the proviso
      that either of the amino acid residues at positions 1, 6, 7, 14,
```

15 and 18 is Ala or citrulline or that the single amino acid that
may be present at position 8 is D-citrulline, citrulline, D-Ala or
Ala
<220> FEATURE:
<223> OTHER INFORMATION: see specification as filed for detailed
description of substitutions and preferred embodiments

<400> SEQUENCE: 24

Xaa Arg Xaa Cys Tyr Xaa Lys Xaa Xaa Gly Xaa Xaa Tyr Xaa Xaa
 1               5                  10                  15

Cys Arg

<210> SEQ ID NO 25
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: hydrogen atom, arginine, lysine, ornithine,
citrulline or alanine residue or a residue of N-a-substituted
derivative of these amino acids
<220> FEATURE:
<221> NAME/KEY: misc_feature
<222> LOCATION: (3)..(3)
<223> OTHER INFORMATION: naphthylalanine
<220> FEATURE:
<221> NAME/KEY: misc_feature
<222> LOCATION: (8)..(9)
<223> OTHER INFORMATION: D-lysyl-proline
<220> FEATURE:
<221> NAME/KEY: misc_feature
<222> LOCATION: (12)..(12)
<223> OTHER INFORMATION: citrulline

<400> SEQUENCE: 25

Xaa Arg Xaa Cys Tyr Arg Lys Xaa Xaa Tyr Arg Xaa Cys Arg
 1               5                  10

<210> SEQ ID NO 26
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: hydrogen atom, arginine, lysine, ornithine,
citrulline or alanine residue or a residue of N-a-substituted
derivative of these amino acids
<220> FEATURE:
<221> NAME/KEY: misc_feature
<222> LOCATION: (3)..(3)
<223> OTHER INFORMATION: naphthylalanine
<220> FEATURE:
<221> NAME/KEY: misc_feature
<222> LOCATION: (8)..(9)
<223> OTHER INFORMATION: D-citrullyl proline
<220> FEATURE:
<221> NAME/KEY: misc_feature
<222> LOCATION: (11)..(11)
<223> OTHER INFORMATION: arg, ala or citrulline residue
<220> FEATURE:
<221> NAME/KEY: misc_feature
<222> LOCATION: (12)..(12)
<223> OTHER INFORMATION: citrulline

<400> SEQUENCE: 26

Xaa Arg Xaa Cys Tyr Arg Lys Xaa Xaa Tyr Xaa Xaa Cys Arg
 1               5                  10

```
<210> SEQ ID NO 27
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: hydrogen atom, arginine, lysine, ornithine,
      citrulline or alanine residue or a residue of N-a-substituted
      derivative of these amino acids
<220> FEATURE:
<221> NAME/KEY: misc_feature
<222> LOCATION: (3)..(3)
<223> OTHER INFORMATION: naphthylalanine
<220> FEATURE:
<221> NAME/KEY: misc_feature
<222> LOCATION: (6)..(6)
<223> OTHER INFORMATION: citrulline
<220> FEATURE:
<221> NAME/KEY: misc_feature
<222> LOCATION: (8)..(9)
<223> OTHER INFORMATION: D-citrullyl proline
<220> FEATURE:
<221> NAME/KEY: misc_feature
<222> LOCATION: (11)..(11)
<223> OTHER INFORMATION: arg, ala or citrulline residue
<220> FEATURE:
<221> NAME/KEY: misc_feature
<222> LOCATION: (12)..(12)
<223> OTHER INFORMATION: citrulline

<400> SEQUENCE: 27

Xaa Arg Xaa Cys Tyr Xaa Lys Xaa Xaa Tyr Xaa Xaa Cys Arg
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Formula peptide
<220> FEATURE:
<221> NAME/KEY: MOD_RES
<222> LOCATION: (1)
<223> OTHER INFORMATION: Arg, Lys, Ala, ornithine, citrulline, any
      derivative of these amino acids, or not present
<220> FEATURE:
<221> NAME/KEY: MOD_RES
<222> LOCATION: (3)
<223> OTHER INFORMATION: Any aromatic amino acid
<220> FEATURE:
<221> NAME/KEY: MOD_RES
<222> LOCATION: (6)..(7)
<223> OTHER INFORMATION: Arg, Lys, Ala, ornithine or citrulline
<220> FEATURE:
<221> NAME/KEY: MOD_RES
<222> LOCATION: (8)
<223> OTHER INFORMATION: Ala, Val, Leu, Ile, Ser, Cys or Met
<220> FEATURE:
<221> NAME/KEY: MOD_RES
<222> LOCATION: (9)
<223> OTHER INFORMATION: Any aromatic amino acid
<220> FEATURE:
<221> NAME/KEY: MOD_RES
<222> LOCATION: (10)
<223> OTHER INFORMATION: Arg, Lys, Ala, ornithine or citrulline
<220> FEATURE:
<221> NAME/KEY: MOD_RES
<222> LOCATION: (12)
<223> OTHER INFORMATION: Tyr, Phe, Trp, Ala, Val, Leu, Ile, Ser, Cys or
      Met; see specification as filed for detailed description of
      substitutions and preferred embodiments
<220> FEATURE:
```

```
-continued

<221> NAME/KEY: DISULFID
<222> LOCATION: (8)..(13)
<223> OTHER INFORMATION: when positions 8 and 13 are Cys, they may form a
      disulfide bond
<220> FEATURE:
<221> NAME/KEY: DISULFID
<222> LOCATION: (4)..(12)
<223> OTHER INFORMATION: when position 12 is Cys, a disulfide bond may be
      formed with the Cys at position 4
<220> FEATURE:
<221> NAME/KEY: MISC_FEATURE
<222> LOCATION: (8)..(13)
<223> OTHER INFORMATION: according to the specification as filed, this
      range may be encompassed by a single residue containing a
      D-citrulline, D-Ala, citrulline or Ala
<220> FEATURE:
<221> NAME/KEY: MOD_RES
<222> LOCATION: (13)
<223> OTHER INFORMATION: Ala, Val, Leu, Ile, Ser, Cys or Met
<220> FEATURE:
<221> NAME/KEY: MOD_RES
<222> LOCATION: (14)
<223> OTHER INFORMATION: Tyr, Phe, Ala, naphthylalanine or citrulline
<220> FEATURE:
<221> NAME/KEY: MOD_RES
<222> LOCATION: (15)
<223> OTHER INFORMATION: Arg, Lys, Ala, ornithine or citrulline
<220> FEATURE:
<221> NAME/KEY: MOD_RES
<222> LOCATION: (16)
<223> OTHER INFORMATION: citrulline
<220> FEATURE:
<221> NAME/KEY: MOD_RES
<222> LOCATION: (18)
<223> OTHER INFORMATION: Lys or Arg; a carboxyl is amidated
<220> FEATURE:
<221> NAME/KEY: MISC_FEATURE
<222> LOCATION: (1)..(18)
<223> OTHER INFORMATION: this sequence is structured with the proviso
      that either of the amino acid residues at positions 1, 6, 7, 14,
      15 and is Ala or citrulline or that the single amino acid that may
      be present at position 8 is D-citrulline, citrulline, D-Ala or Ala
<220> FEATURE:
<223> OTHER INFORMATION: see specification as filed for detailed
      description of substitutions and preferred embodiments

<400> SEQUENCE: 28

Xaa Arg Xaa Cys Tyr Xaa Xaa Xaa Xaa Xaa Gly Xaa Xaa Xaa Xaa Xaa
 1               5                  10                  15

Cys Xaa
```

The invention claimed is:

1. A polypeptide or salt thereof represented by one of the following formulas:

Ala-Arg-Nal-Cys-Tyr-Arg-Lys-DLys-Pro-Tyr-Arg-Cit-Cys-Arg (SEQ ID NO: 3);

Arg-Arg-Nal-Cys-Tyr-Ala-Lys-DLys-Pro-Tyr-Arg-Cit-Cys-Arg (SEQ ID NO: 4);

Arg-Arg-Nal-Cys-Tyr-Arg-Ala-DLys-Pro-Tyr-Arg-Cit-Cys-Arg (SEQ ID NO: 5);

Arg-Arg-Nal-Cys-Tyr-Arg-Lys-DAla-Pro-Tyr-Arg-Cit-Cys-Arg (SEQ ID NO: 6);

Arg-Arg-Nal-Cys-Tyr-Arg-Lys-DLys-Ala-Tyr-Arg-Cit-Cys-Arg (SEQ ID NO: 7);

Arg-Arg-Nal-Cys-Tyr-Arg-Lys-DLys-Pro-Ala-Arg-Cit-Cys-Arg (SEQ ID NO: 8);

Arg-Arg-Nal-Cys-Tyr-Arg-Lys-DLys-Pro-Tyr-Ala-Cit-Cys-Arg (SEQ ID NO: 9);

Cit-Arg-Nal-Cys-Tyr-Arg-Lys-DLys-Pro-Tyr-Arg-Cit-Cys-Arg (SEQ ID NO: 10);

Arg-Arg-Nal-Cys-Tyr-Arg-Cit-DLys-Pro-Tyr-Arg-Cit-Cys-Arg (SEQ ID NO: 12);

Arg-Arg-Nal-Cys-Tyr-Arg-Lys-DLys-Pro-Tyr-Cit-Cit-Cys-Arg (SEQ ID NO: 14);

Cit-Arg-Nal-Cys-Tyr-Arg-Lys-DCit-Pro-Tyr-Arg-Cit-Cys-A7, wherein A7 represents an arginine residue in which a carboxyl group is amidated (SEQ ID NO: 16); or Arg-Arg-Nal-Cys-Tyr-Arg-Lys-DCit-Pro-Tyr-Arg-Cit-Cys-Arg (SEQ ID NO: 21).

2. The polypeptide according to claim 1 or a salt thereof, wherein said polypeptide is represented by the following formula:

Ala-Arg-Nal-Cys-Tyr-Arg-Lys-DLys-Pro-Tyr-Arg-Cit-Cys-Arg (SEQ ID NO: 3).

3. The polypeptide according to claim 1 or a salt thereof, wherein said polypeptide is represented by the following formula:

Arg-Arg-Nal-Cys-Tyr-Ala-Lys-DLys-Pro-Tyr-Arg-Cit-Cys-Arg (SEQ ID NO: 4).

4. The polypeptide according to claim 1 or a salt thereof, wherein said polypeptide is represented by the following formula:

Arg-Arg-Nal-Cys-Tyr-Arg-Ala-DLys-Pro-Tyr-Arg-Cit-Cys-Arg (SEQ ID NO: 5).

5. The polypeptide according to claim 1 or a salt thereof, wherein said polypeptide is represented by the following formula:

Arg-Arg-Nal-Cys-Tyr-Arg-Lys-DAla-Pro-Tyr-Arg-Cit-Cys-Arg (SEQ ID NO: 6).

6. The polypeptide according to claim 1 or a salt thereof, wherein said polypeptide is represented by the following formula:

Arg-Arg-Nal-Cys-Tyr-Arg-Lys-DLys-Ala-Tyr-Arg-Cit-Cys-Arg (SEQ ID NO: 7).

7. The polypeptide according to claim 1 or a salt thereof, wherein said polypeptide is represented by the following formula:

Arg-Arg-Nal-Cys-Tyr-Arg-Lys-DLys-Pro-Ala-Arg-Cit-Cys-Arg (SEQ ID NO: 8).

8. The polypeptide according to claim 1 or a salt thereof, wherein said polypeptide is represented by the following formula:

Arg-Arg-Nal-Cys-Tyr-Arg-Lys-DLys-Pro-Tyr-Ala-Cit-Cys-Arg (SEQ ID NO: 9).

9. The polypeptide according to claim 1 or a salt thereof, wherein said polypeptide is represented by the following formula:

Cit-Arg-Nal-Cys-Tyr-Arg-Lys-DLys-Pro-Tyr-Arg-Cit-Cys-Arg (SEQ ID NO: 10).

10. The polypeptide according to claim 1 or a salt thereof, wherein said polypeptide is represented by the following formula:

Arg-Arg-Nal-Cys-Tyr-Arg-Cit-DLys-Pro-Tyr-Arg-Cit-Cys-Arg (SEQ ID NO: 12).

11. The polypeptide according to claim 1 or a salt thereof, wherein said polypeptide is represented by the following formula:

Arg-Arg-Nal-Cys-Tyr-Arg-Lys-DLys-Pro-Tyr-Cit-Cit-Cys-Arg (SEQ ID NO: 14).

12. The polypeptide according to claim 1 or a salt thereof, wherein said polypeptide is represented by the following formula:

Cit-Arg-Nal-Cys-Tyr-Arg-Lys-DCit-Pro-Tyr-Arg-Cit-Cys-A7, wherein A7 represents an arginine residue in which a carboxyl group is amidated (SEQ ID NO: 16).

13. The polypeptide according to claim 1 or a salt thereof, wherein said polypeptide is represented by the following formula:

Arg-Arg-Nal-Cys-Tyr-Arg-Lys-DCit-Pro-Tyr-Arg-Cit-Cys-Arg (SEQ ID NO: 21).

14. A complex comprising a polypeptide or a salt thereof according to claim 1 to which a reverse transcriptase inhibitor, an HIV protease inhibitor, or an in vivo half-time elongating substance is bound.

15. A pharmaceutical composition comprising a polypeptide or a salt thereof according to claim 1 as an effective ingredient.

16. The polypeptide according to claim 1 or a salt thereof, wherein a hydrogen atom of a side chain w-amino group of D-arginine, L-arginine, D-lysine, L-lysine, D-ornithine or L-ornithine may be substituted by a w-aminoacyl group; and the cysteine residues at the 4-position and the 13-position may be bonded by a disulfide bond.

17. A complex comprising a polypeptide or a salt thereof according to claim 16 to which a reverse transcriptase inhibitor, an HIV protease inhibitor, or an in vivo half-time elongating substance is bound.

18. A pharmaceutical composition comprising a polypeptide or a salt thereof according to claim 16 as an effective ingredient.

\* \* \* \* \*